US012579682B2

(12) United States Patent
Hu et al.

(10) Patent No.: US 12,579,682 B2
(45) Date of Patent: Mar. 17, 2026

(54) THREE-DIMENSIONAL REAL-TIME POSITIONING COMPENSATION METHOD FOR SURGERY

(71) Applicant: METAL INDUSTRIES RESEARCH & DEVELOPMENT CENTRE, Kaohsiung (TW)

(72) Inventors: Po-Chi Hu, Kaohsiung (TW); Chin-Chung Lin, Kaohsiung (TW); Chieh-Hua Chen, Kaohsiung (TW); Wen-Hui Huang, Kaohsiung (TW); Yan-Ting Chen, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 301 days.

(21) Appl. No.: 18/515,237

(22) Filed: Nov. 20, 2023

(65) Prior Publication Data

US 2025/0166221 A1 May 22, 2025

(51) Int. Cl.
*G06T 7/73* (2017.01)
*A61B 34/20* (2016.01)
(Continued)

(52) U.S. Cl.
CPC ................ *G06T 7/73* (2017.01); *A61B 34/20* (2016.02); *G06T 3/40* (2013.01); *G06T 5/92* (2024.01);
(Continued)

(58) Field of Classification Search
CPC .... G06T 7/73; G06T 5/92; G06T 3/40; G06T 2207/20016; G06T 2207/30004; G06T 2207/30204; A61B 34/20
See application file for complete search history.

(56) References Cited

U.S. PATENT DOCUMENTS

| 12,042,341 | B2 * | 7/2024 | Poltaretskyi | ........... A61B 90/36 |
| 2021/0174950 | A1 * | 6/2021 | Hu | ........................ A61B 17/846 |

(Continued)

FOREIGN PATENT DOCUMENTS

| TW | 1708591 B | 11/2020 | |
| WO | WO-2024254421 A1 * | 12/2024 | ............. A61B 90/94 |

OTHER PUBLICATIONS

Koeda, Masanao, et al. "Development of wireless surgical knife attachment with proximity indicators using ArUco marker." International Conference on Human-Computer Interaction. Cham: Springer International Publishing, 2018. (Year: 2018).*

*Primary Examiner* — Utpal D Shah
(74) *Attorney, Agent, or Firm* — Juan Carlos A. Marquez; Marquez IP Law Office, PLLC

(57) ABSTRACT

A three-dimensional real-time positioning compensation method for surgery includes: obtaining an initial posture of each of a plurality of marking devices in a surgical image in a world coordinate system; performing brightness normalization on the surgical image to generate a normalized image; respectively generating a plurality of texture images with different resolutions for all marks of the plurality of marking devices, and using the texture image having the closest resolution as a standard image; selecting at least N additional sampling points from the standard image, and obtaining a corresponding reference point in the normalized image; and obtaining an optimization point with a minimum brightness error from each reference point, respectively performing a calculation to obtain an error; and correcting the initial posture according to the errors to generate a compensation posture.

4 Claims, 4 Drawing Sheets

(51) Int. Cl.
  *G06T 3/40* (2024.01)
  *G06T 5/92* (2024.01)

(52) U.S. Cl.
  CPC .............. *G06T 2207/20016* (2013.01); *G06T 2207/30004* (2013.01); *G06T 2207/30204* (2013.01)

(56) References Cited

U.S. PATENT DOCUMENTS

| | | | |
|---|---|---|---|
| 2021/0346117 A1* | 11/2021 | Poltaretskyi | A61B 90/36 |
| 2022/0172445 A1* | 6/2022 | Chen | G06T 19/20 |
| 2023/0263541 A1* | 8/2023 | Roussouly | A61B 17/1703 |
| 2024/0041558 A1* | 2/2024 | Siewerdsen | A61B 90/94 |
| 2024/0189042 A1* | 6/2024 | Fouts | A61B 17/1703 |
| 2024/0358445 A1* | 10/2024 | Murphy | A61B 17/02 |
| 2024/0374318 A1* | 11/2024 | Fouts | A61B 34/20 |
| 2025/0098942 A1* | 3/2025 | Godbey | G16H 40/40 |
| 2025/0120785 A1* | 4/2025 | Halverson | A61B 90/10 |
| 2025/0204999 A1* | 6/2025 | Miga | A61B 34/32 |

* cited by examiner

THREE-DIMENSIONAL REAL-TIME POSITIONING COMPENSATION METHOD FOR SURGERY

BACKGROUND

Technical Field

The present disclosure mainly relates to a three-dimensional real-time positioning compensation method for surgery, and in particular, to a three-dimensional real-time positioning compensation method implemented by increasing a quantity of sampling points and correcting a trackball posture with image brightness and actual brightness.

Related Art

In recent years, with development of computer-aided positioning technologies, medical personnel can use imaging equipment to obtain a two-dimensional image of a lesion position of a patient during a precise surgical operation such as orthopedics or spine, use a computer to reconstructs a three-dimensional image of the lesion according to the two-dimensional image, and then coordinates the lesion. The medical personnel can then accurately implant an implant into a correct position under the guidance of the computer. This has the advantage of greatly improving the accuracy of surgical positioning.

Patent document (Patent No. TW 1708591) discloses a three-dimensional real-time positioning method for orthopedic surgery. According to this method, a three-dimensional marking device is fixed on a surgical site, and a camera is set up to shoot and obtain a captured image. Subsequently, the captured image is identified to obtain positions of two-dimensional corner points of the three-dimensional marking device. However, the captured image includes pixels. The pixels appear granular at a microscopic level and produce image gradients at boundaries. Even if the three-dimensional marking device in the captured image is in a stationary state, the two-dimensional corner points still produce an error of ±3 pixels, leading to a large error in calculating a posture of the three-dimensional marking device, and thus resulting in poor accuracy.

In view of this, it is necessary to provide a three-dimensional real-time positioning compensation method for surgery to solve the foregoing problem.

SUMMARY

The objective of the present disclosure is to provide a three-dimensional real-time positioning compensation method implemented by increasing a quantity of sampling points and correcting a trackball posture with image brightness and actual brightness.

The "mechanical corner point" described in the present disclosure refers to actual coordinates of four corners of a graphic of each mark on a regular polyhedron relative to a central origin of the regular polyhedron of a marking device.

To achieve the foregoing objective, the present disclosure provides a three-dimensional real-time positioning compensation method for surgery, including: obtaining a surgical image, wherein the surgical image comprises a plurality of marking devices, the marking device has a regular polyhedron, the regular polyhedron has at least four geometric faces, the geometric face has a mark, the mark comprises a frame and a graphic, and the graphic is located inside the frame and is used for identification to obtain a unique identification code; inputting the surgical image into an object detection model to detect first bounding box information of each of the plurality of marking devices, second bounding box information of the frame of each marking device, and an identification code and third bounding box information represented by the graphic of each marking device; obtaining four corner points of the corresponding frame according to the second bounding box information, and performing a first projection transformation calculation according to the first bounding box information of each of the plurality of marking devices, the four corner points of the frame and corresponding mechanical corner points, to obtain an initial posture of each of the plurality of marking devices in a world coordinate system; performing brightness normalization on the surgical image to generate a normalized image; respectively generating a plurality of texture images having equal ratio of length to width but having different resolutions for all marks of the plurality of marking devices; respectively performing a fuzzy logic operation on the different resolutions of the plurality of texture images with the same identification code according to the identification code represented by the graphic of each marking device, and using the texture image having the closest resolution as a standard image; selecting at least N sampling points other than the four corner points from a frame or a graphic of the standard image according to the second bounding box information and the third bounding box information, performing a second projection transformation calculation according to the at least N sampling points and corresponding mechanical corner points, and performing a calculation based on a camera parameter, to obtain a reference point corresponding to each of the at least N sampling points in the normalized image, wherein N is a positive integer; obtaining an optimization point within an allowable range by using the reference point as an origin, wherein there is a minimum brightness error between the optimization point and the reference point; calculating an error between each reference point and the corresponding optimization point based on a minimization error function, and correcting the initial posture according to the error to generate a compensation posture; and respectively drawing and displaying a compensation posture of each of the plurality of marking devices in the world coordinate system on a display screen in real time.

In some embodiments, $100 \leq N \leq 300$.

In some embodiments, the allowable range is ±1 pixel.

In some embodiments, the object detection model is YoLov5.

The three-dimensional real-time positioning compensation method in the present disclosure has the following characteristics: A quantity of sampling points on the frame or the graphics of the mark is increased, and a minimum error between the image brightness of the sampling points and the actual brightness is used to correct the posture of each of the plurality of marking devices in the world coordinate system. Therefore, according to the three-dimensional real-time positioning compensation method of the present disclosure, after ASTM F2554 is used for accuracy verification, an average error of the marking device drops from 0.8547 to 0.1493. This can achieve the effect of improving and stabilizing the positioning accuracy of the marking device.

DETAILED DESCRIPTION

Figure 1:
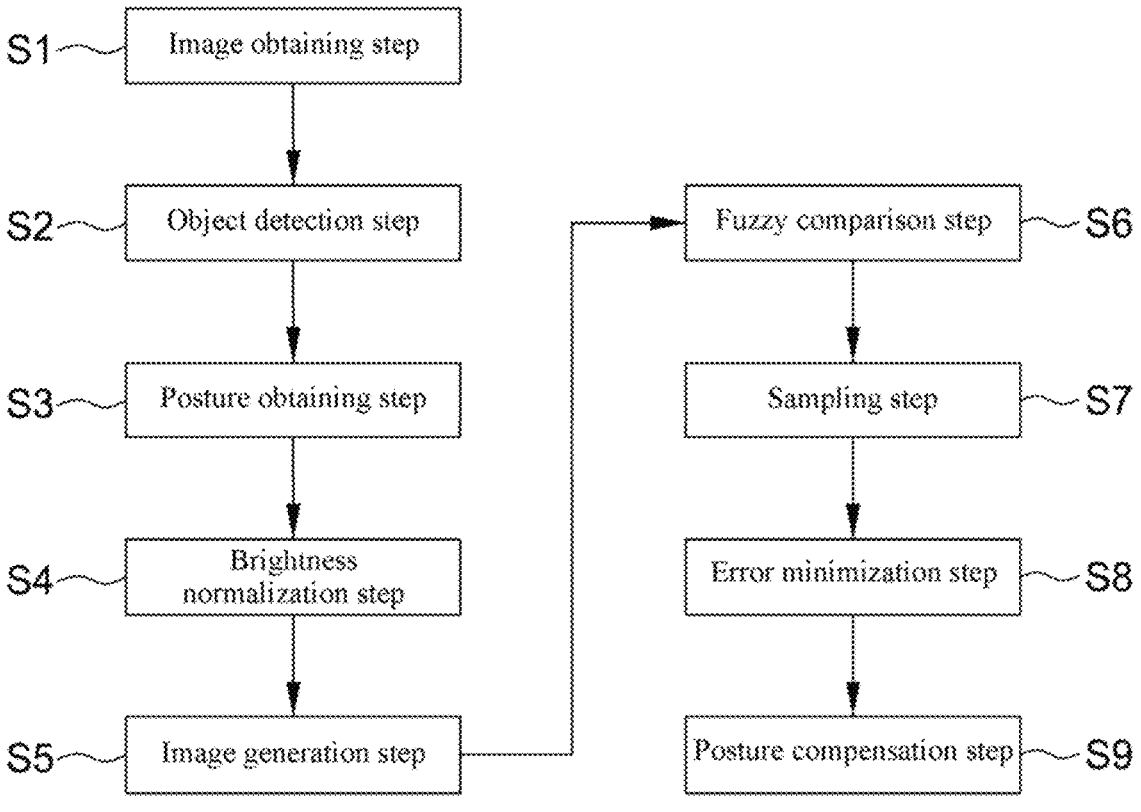
FIG. 1 is a flowchart of a three-dimensional real-time positioning compensation method according to the present disclosure.

Embodiments of the present disclosure are described in detail below with reference to the accompanying drawings. The accompanying drawings are mainly simplified schematic diagrams, and only illustrate the basic structure of the present disclosure in a schematic manner. Therefore, only elements related to the present disclosure are marked in these drawings, and the elements shown are not drawn based on a quantity, a shape, a size ratio, and the like during actual implementation. Specifications and sizes during actual implementation are actually selective designs, and the element layout may be more complex.

The following description of various embodiments is provided to exemplify the specific embodiments of the present disclosure with reference to accompanying drawings. The directional terms described in the present disclosure, for example, "upper", "lower", "before", and "after" are only references to the directions in the drawings. Therefore, the used direction terms are intended to describe and understand the present disclosure, but are not intended to limit the present disclosure. In addition, in the specification, unless expressly described to the contrary, the term "including" is to be understood to mean the inclusion of stated elements but not the exclusion of any other elements.

Figure 2:
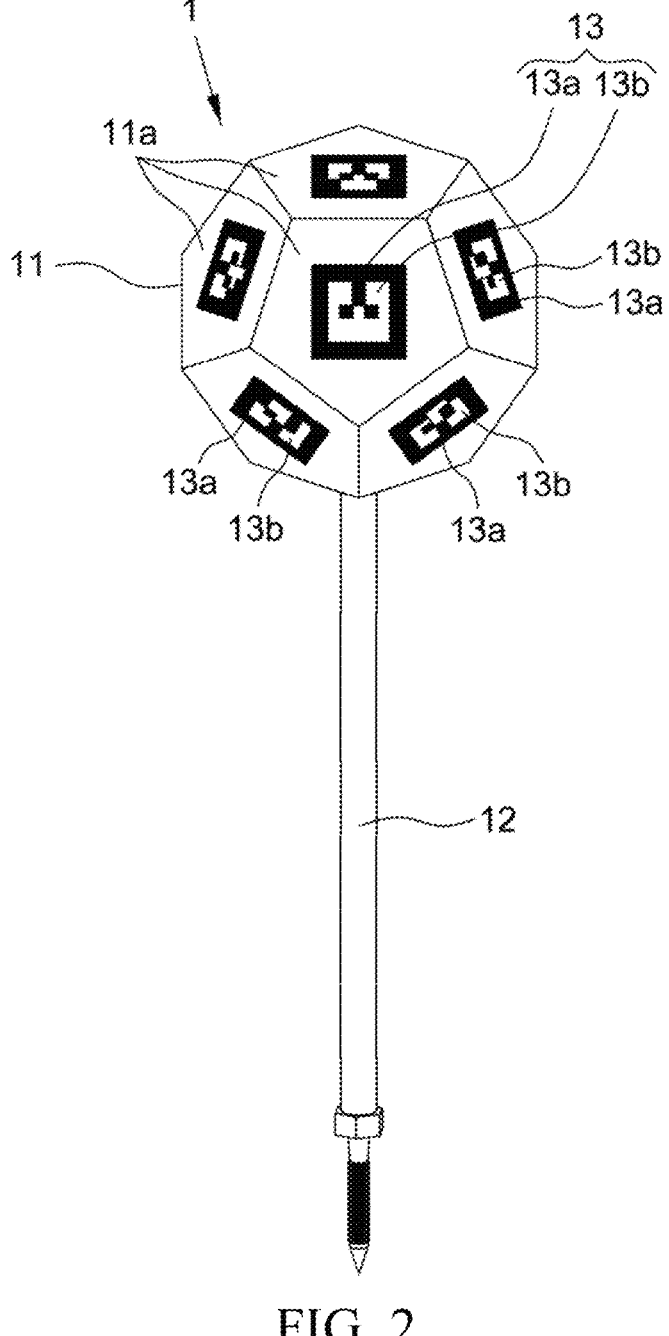
FIG. 2 is a three-dimensional view of a marking device for a three-dimensional real-time positioning compensation method according to the present disclosure.

FIG. 1 is a flowchart of a three-dimensional real-time positioning compensation method according to the present disclosure, and the three-dimensional real-time positioning compensation method for surgery includes the following steps:

Refer to FIG. 2. Image obtaining step S1: Obtain a surgical image. The surgical image includes a plurality of marking devices 1. In this embodiment, the marking device 1 is a tracking ball and uses a rigid dodecahedral sphere. Specifically, the marking device 1 has a regular polyhedron 11 and a nail-shaped body 12. The regular polyhedron 11 has at least four geometric faces 11a showing a regular pentagon, the geometric face 11a has a mark 13, the mark 13 includes a frame 13a and a graphic 13b, and the graphic 13b is located inside the frame 13a and is used for identification to obtain a unique identification code. For example, the mark 13 may be one of an AR-ToolKit mark, an ARTag mark, an ArUco mark, or an AlVar mark. In this embodiment, the AlVar mark is used as the mark 13 on the geometric face 11a. The nail-shaped body 12 is used to fix the marking device 1 to at least one surgical site of a surgical instrument or a patient/teaching aid.

Figure 3:
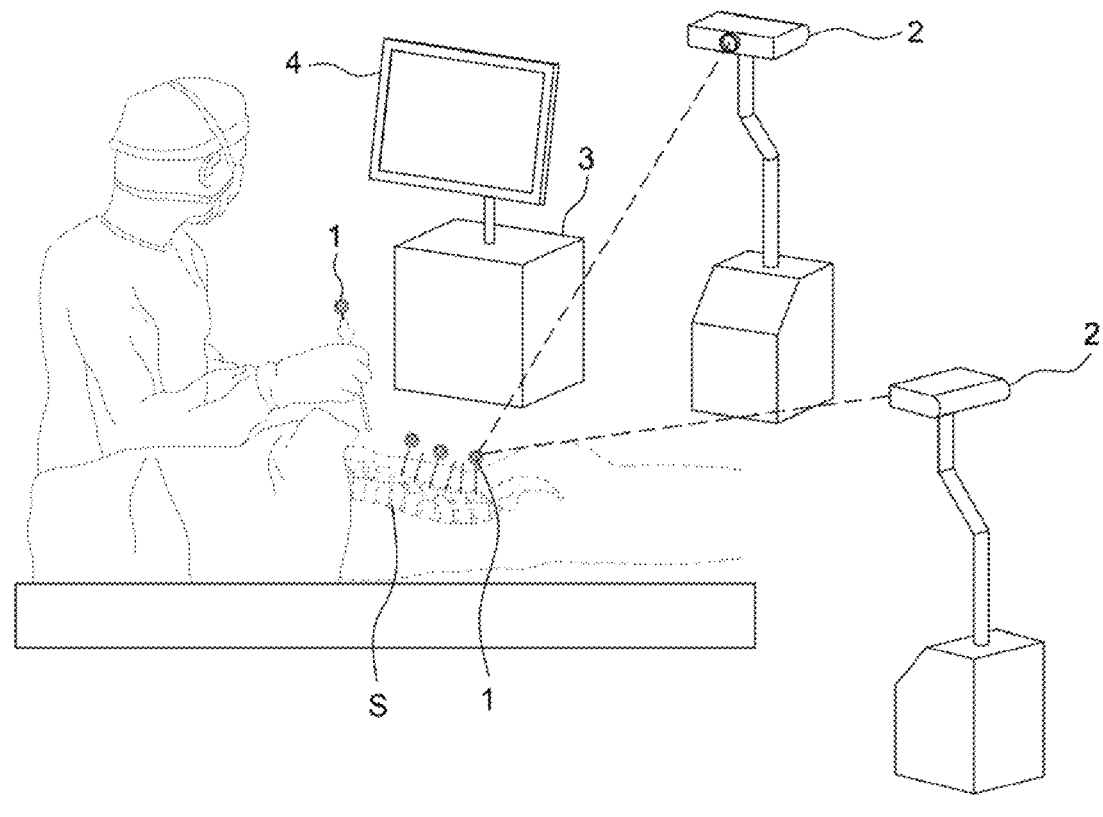
FIG. 3 is a usage diagram of a three-dimensional real-time positioning compensation method according to the present disclosure.

Refer to FIG. 3. When the surgical site is a spine S, the nail-shaped body 12 is a spinal process nail, and can be understood by those with ordinary knowledge in the technical field of the present disclosure. It is worth noting that the plurality of marking devices 1 do not have graphics 13b with the same identification code. For example, the identification code represented by the graphic 13b of the mark 13 of the marking device 1 of the surgical instrument may be 0 to 8, and the identification codes represented by the graphics 13b of the marks 13 of the three marking devices 1 disposed on the spine may be 9 to 17, 18 to 26, and 27 to 35 by analogy. It is worth mentioning that when the marking device 1 is inserted into the surgical site, three geometric faces 11a face downward toward the surgical site and cannot be recognized. Therefore, the identification codes represented by the graphics 13b of the marks 13 may be set to 9 mark numbers.

Based on the above, in the present disclosure, at least one camera 2 is set up and shooting is performed toward the plurality of marking devices 1 to generate the surgical image. In this embodiment, the camera 2 is a camera with a high image quality function and six degree of freedom (DOF) motion postures.

Object detection step S2: Input the surgical image into an object detection model in a computer host 3 to detect first bounding box information of each of the plurality of marking devices 1, second bounding box information of the frame 13a of each marking device 1, and an identification code and third bounding box information represented by the graphic 13b of each marking device 1. In this embodiment, the identification codes represented by the graphics 13b of at least three marks 13 of the marking devices 1 can be recognized, improving positioning accuracy.

In the present disclosure, the object detection model can download a deep learning model completing parameter settings from the Internet to the computer host 3. Under the C++ development environment, the computer host 3 trains the deep learning model based on a plurality of previously taken surgical images to obtain the object detection model. In this embodiment, YoLov5 is used for illustration, and belongs to common knowledge in the technical field of the present disclosure. Details are not described herein again.

Posture obtaining step S3: Obtain four corner points of the corresponding frame 13a according to the second bounding box information; and perform a first projection transformation calculation according to the first bounding box information of each of the plurality of marking devices 1, the four corner points of the frame 13a and corresponding mechanical corner points, to obtain an initial posture of each of the plurality of marking devices 1 in a world coordinate system. In this embodiment, the computer host 3 can complete the calculation by calling a solvepnp( ) function in an OpenCV computer vision library. This is common knowledge in the relevant fields of the present disclosure. Details are not described herein again.

Brightness normalization step S4: Perform brightness normalization on the surgical image to generate a normalized image. For example, the standard image can be converted into a brightness histogram in a contrast stretching manner, and then evenly stretched to a brightness range of 0 to 255.

Image generation step S5: Respectively generate a plurality of texture images having equal ratio of length to width but having different resolutions for all marks 13 of the plurality of marking devices 1. In this embodiment, the original image resolution of the surgical image captured by the camera 2 is 640*640. The computer host 3 performs image processing methods such as reduction, enlargement, and blurring on the surgical image to generate a plurality of texture images with different resolutions of 320*320, 160*160, 80*80, 40*40, 20*20, and 10*10 respectively.

Fuzzy comparison step S6: Respectively perform a fuzzy logic operation on the different resolutions of the plurality of texture images with the same identification code according to the identification code represented by the graphic 13b of each marking device 1, and use the texture image having the closest resolution as a standard image. In this embodiment, the fuzzy logic operation is a calculation using an energy gradient function.

Figure 4:
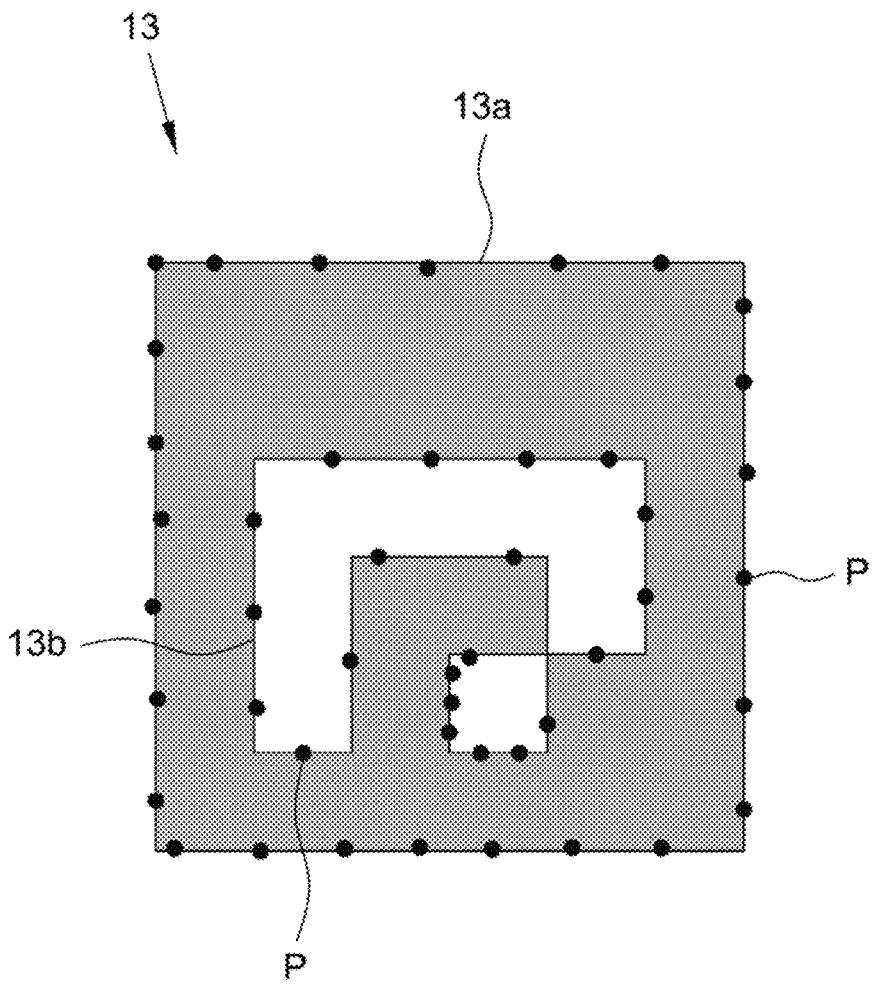
FIG. 4 shows sampling points of a three-dimensional real-time positioning compensation method according to the present disclosure.

FIG. 4 shows sampling points of a frame and a graphic of the standard image. Refer to FIG. 4. Sampling step S7: Select at least N sampling points P other than the four corner points from a frame 13*a* or a graphic 13*b* of the standard image according to the second bounding box information and the third bounding box information, wherein in this embodiment, N is a positive integer, and 100≤N≤300; perform a second projection transformation calculation according to the at least N sampling points P and corresponding mechanical corner points; and perform a calculation based on a camera parameter of the camera 2, to obtain a reference point corresponding to each of the at least N sampling points P in the normalized image. The camera parameter of the camera 2 belongs to common knowledge in the technical field of the present disclosure.

Error minimization step S8: Obtain an optimization point within an allowable range by using the reference point as an origin, where there is a minimum brightness error between the optimization point and the reference point. The allowable range can be ±1 pixel, and a formula of the brightness error may be as shown below and belongs to common knowledge in the technical field of the present disclosure.

$$E(p) = \frac{1}{n}\sum_{i=1}^{n}(I_c(u_i(p)) - O_t(x_i))^2.$$

An error between each reference point and the corresponding optimization point is then calculated based on a minimization error function, and the initial posture is corrected according to the error to generate a compensation posture. The minimization error function may be as shown below, and belongs to common knowledge in the technical field of the present disclosure.

$$\Delta p^* = \operatorname*{argmin}_{\Delta p}\frac{1}{n}\sum_{i=1}^{n}(I_c(u_i(p' + \Delta p)) - O_t(x_i))^2.$$

Posture compensation step S9: Respectively draw and display a compensation posture of each of the plurality of marking devices 1 in the world coordinate system on a display screen 4 in real time.

Based on the above, according to the three-dimensional real-time positioning compensation method in the present disclosure, a quantity of sampling points on the frame or the graphics of the mark is increased, and a minimum error between the image brightness of the sampling points and the actual brightness is used to correct the posture of each of the plurality of marking devices in the world coordinate system. Therefore, according to the three-dimensional real-time positioning compensation method of the present disclosure, after ASTM F2554 is used for accuracy verification, an average error of the marking device drops from 0.8547 to 0.1493. This can achieve the effect of improving and stabilizing the positioning accuracy of the marking device.

The above-disclosed embodiments are only illustrative of the principles, characteristics, and effects of the present disclosure, and are not intended to limit the scope of the present disclosure. Any person skilled in this art can modify and change the above embodiments without departing from the spirit and scope of the present disclosure. Any equivalent changes and modifications accomplished by applying the contents disclosed in the present disclosure shall still be covered by the following patent application scope.

What is claimed is:

1. A three-dimensional real-time positioning compensation method for surgery, comprising:

obtaining a surgical image, wherein the surgical image comprises a plurality of marking devices, the marking device has a regular polyhedron, the regular polyhedron has at least four geometric faces, the geometric face has a mark, the mark comprises a frame and a graphic, and the graphic is located inside the frame and is used for identification to obtain a unique identification code;

inputting the surgical image into an object detection model to detect first bounding box information of each of the plurality of marking devices, second bounding box information of the frame of each marking device, and an identification code and third bounding box information represented by the graphic of each marking device;

obtaining four corner points of the corresponding frame according to the second bounding box information, and performing a first projection transformation calculation according to the first bounding box information of each of the plurality of marking devices, the four corner points of the frame and corresponding mechanical corner points, to obtain an initial posture of each of the plurality of marking devices in a world coordinate system;

performing brightness normalization on the surgical image to generate a normalized image;

respectively generating a plurality of texture images having equal ratio of length to width but having different resolution for all marks of the plurality of marking devices;

respectively performing a fuzzy logic operation on the different resolutions of the plurality of texture images with the same identification code according to the identification code represented by the graphic of each marking device, and using the texture image having the closest resolution as a standard image;

selecting at least N sampling points other than the four corner points from a frame or a graphic of the standard image according to the second bounding box information and the third bounding box information, performing a second projection transformation calculation according to the at least N sampling points and corresponding mechanical corner points, and performing a calculation based on a camera parameter, to obtain a reference point corresponding to each of the at least N sampling points in the normalized image, wherein N is a positive integer;

obtaining an optimization point within an allowable range by using the reference point as an origin, wherein there is a minimum brightness error between the optimization point and the reference point; calculating an error between each reference point and the corresponding optimization point based on a minimization error function, and correcting the initial posture according to the error to generate a compensation posture; and respectively drawing and displaying a compensation posture of each of the plurality of marking devices in the world coordinate system on a display screen in real time.

2. The three-dimensional real-time positioning compensation method for surgery according to claim 1, wherein 100≤N≤300.

3. The three-dimensional real-time positioning compensation method for surgery according to claim 1, wherein the allowable range is ±1 pixel.

4. The three-dimensional real-time positioning compensation method for surgery according to claim 1, wherein the object detection model is YoLov5.

* * * * *